United States Patent [19]

DiMarchi et al.

[11] Patent Number: 4,617,149

[45] Date of Patent: Oct. 14, 1986

[54] GROWTH HORMONE RELEASE FACTOR ANALOGS

[75] Inventors: Richard D. DiMarchi, Carmel; Carl J. Shaar, Indianapolis, both of Ind.

[73] Assignee: Eli Lilly and Company, Indianapolis, Ind.

[21] Appl. No.: 534,518

[22] Filed: Sep. 21, 1983

[51] Int. Cl.$^4$ .............................................. C07K 7/10
[52] U.S. Cl. .................................................. 530/324
[58] Field of Search .................. 260/112.5 R; 424/177

[56] References Cited

U.S. PATENT DOCUMENTS 4,529,595  7/1985  Rivier et al. ................ 260/112.5 R

FOREIGN PATENT DOCUMENTS 117034  6/1984  European Pat. Off. .

OTHER PUBLICATIONS

Rivier et al., 8th American Peptides Symposium, Tucson, Arizona, 237 (1983), May 22–27.
R. Guillemin et al., Growth Hormone–Releasing Factor from a Human Pancreatic Tumor that Caused Acromegaly, Science, 218:585–587, 1982.
F. S. Esch et al., Characterization of a 40 Residue Peptide from a Human Pancreatic Tumor with Growth Hormone Releasing Activity, Biochem. Biophys. Res. Comm., 109:152–158, 1982.
J. Rivier et al., Characterization of a Growth Hormone–Releasing Factor from a Human Pancreatic Islet Tumour, Nature, 300:276–278, 1982.
W. B. Wehrenberg et al., Somatocrinin, Growth Hormone Releasing Factor, Stimulates Secretion of Growth Hormone in Anesthetized Rats, Biochem. Biophys. Res. Comm,. 109:382–387, 1982.
P. Brazeau et al., Somatocrinin (Growth Hormone Releasing Factor) In Vitro Bioactivity; Ca++ Involvement, cAMP Mediated Action and Additivity of Effect with PGE$_2$, Biochem. Biophys. Res. Comm., 109:588–594, 1982.
J. Spiess et al., Sequence Analysis of a Growth Hormone Releasing Factor from a Human Pancreatic Islet Tumor, Biochemistry, 21:6037–6040, 1982.
M. O. Thorner et al., Human Pancreatic Growth-Hormone-Releasing Factor Selectively Stimulates Growth-Hormone Secretion in Man, Lancet, Jan. 1/8, pp. 24–28, 1983.
F. S. Esch et al., Primary Structures of Three Human Pancreas Peptides with Growth Hormone–Releasing Activity, J. Biol. Chem., 258:1806–1810, 1983.
A. Arimura et al., In Vitro Pituitary Hormone Releasing Activity of 40 Residue Human Pancreatic Tumor Growth Hormone Releasing Factor, Peptides, 4:107–11–, 1983.
W. A. Murphy et al., Effects of Secretion and Gastric Inhibitory Polypeptide on Human Pancreatic Growth Hormone-Releasing Factor (1–40)-Stimulated Growth Hormone Levels in the Rat, Biochem. Biophys. Res. Comm, 112:469–474, 1983.
W. Vale et al., Effects of Synthetic Human Pancreatic (Tumor) GH Releasing Factor and Somatostatin, Triodothyronine and Dexamethasone on GH Secretion In Vitro, Endocrinology, 112:1553–1555, 1983.

*Primary Examiner*—Donald B. Moyer
*Assistant Examiner*—F. T. Moezie
*Attorney, Agent, or Firm*—William C. Martens

[57] ABSTRACT

A class of compounds having growth hormone releasing activity is described. These compounds have the formula H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-X-Ser-Arg-Gln-Gln-Gly-Glu-Ser-Asn-Gln-Glu-Arg-Gly-Ala-Arg-Ala-Arg-Leu-Y in which Y is OH or NH$_2$ and X is selected from the group consisting of Met(O), Met(S-Me), Hse, Gln, Asn, Ser, Thr, Leu, Ile, Ala, Gly, Pro, Val, Phe, Trp, Tyr, Cys, Lys, Arg, His, Glu, and Asp.

6 Claims, No Drawings

GROWTH HORMONE RELEASE FACTOR ANALOGS

BACKGROUND OF THE INVENTION

A 44 amino acid peptide having growth hormone releasing activity has recently been reported [Guillemin et al., Science 218, 585 (1982)]. The peptide, isolated from a human tumor of the pancreas and designated hpGRF, has the structure H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gpn-Asp-Ile-Met-Ser-Arg-Gln-Gln-Gly-Glu-Ser-Asn-Gln-Glu-Arg-Gly-Ala-Arg-Ala-Arg-Leu-NH$_2$.

At approximately the same time, a shortened form of the foregoing peptide, also having growth hormone releasing activity, was also reported [Rivier et al., Nature 300, 276 (1982)]. This peptide terminates as a free carboxylic acid and differs from the foregoing by the absence of the C-terminal tetrapeptide amide -Arg-Ala-Arg-Leu-NH$_2$.

A study of growth hormone release factor (GRF) (whether the 44 amino acid form or the shortened 40 amino acid form) has established (as its name implies) its efficacy in stimulating pituitary release of growth hormone. It has also been suggested (Rivier et al., supra) that GRF activity is retained even upon further shortening of the C-terminal region of the peptide. Thus, Rivier et al. prepared and tested a number of shortened GRF analogs. When compared in vitro with the parent hpGRF(1-40)-OH, Rivier et al. state that the following exhibited similar (within a factor of two) potencies: hpGRF(1-29)-NH$_2$, hpGRF(1-32)-NH$_2$, hpGRF(1-39)-NH$_2$, and hpGRF(1-40)-NH$_2$. Moreover, they state that "full intrinsic activity is observed in hpGRF(1-27)-NH$_2$ which possesses 10-20% of the potency of hpGRF(1-40)-OH." (page 277).

Rivier et al. further examined the importance of the methionine-27 residue in the overall sequence. They converted hpGRF(1-40)-OH to the corresponding methionine sulfoxide derivative and, upon in vitro testing, conclude that "partial oxidation of methionine-27 to methionine sulfoxide leads to a significant loss of activity (about 2% of that of the parent compound) . . . " (page 276, FIG. 1 legend).

The implicit conclusions of the Rivier et al. studies suggest (1) that much of the C-terminal portion of the hpGRF(1-40)-OH is of only limited importance to the growth hormone releasing activity of the molecule and (2) that the methionine in position 27 is of great importance to such activity.

It has now been discovered that, contrary to the Rivier et al. conclusions, the growth hormone releasing activity of hpGRF is not dependent upon the presence of methionine in position 27. It is to a class of analogs of hpGRF bearing substitutions of the methionine residue that this invention is directed. The compounds of this invention exhibit, upon in vivo administration, high levels of growth hormone releasing activity.

SUMMARY OF THE INVENTION

Thus, this invention is directed to a class of compounds having the formula H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-X-Ser-Arg-Gln-Gln-Gly-Glu-Ser-Asn-Gln-Glu-Arg-Gly-Ala-Arg-Ala-Arg-Leu-Y and pharmaceutically acceptable salts thereof in which Y is OH or NH$_2$ and X is selected from the group consisting of Met(O), Met(S-Me), Hse, Gln, Asn, Ser, Thr, Leu, Ile, Ala, Gly, Pro, Val, Phe, Trp, Tyr, Cys, Lys, Arg, His, Glu, and Asp.

DETAILED DESCRIPTION OF THE INVENTION

As noted, the compounds of this invention are peptides having the general sequence of hpGRF or amino terminal portions thereof, but differing therefrom by replacement of the methionine (Met) residue in position 27 by any of a number of amino acid residues.

The thioether side chain functionality of methionine is susceptible to several modification reactions including oxidation, alkylation, and cyanolation. While selective modification is achievable in the presence of tryptophan, cysteine, and cystine residues, their absence facilitates quantitative derivatization to a homogeneous product. While modification studies can provide a considerable amount of information regarding structure-function relationships, it is quite restrictive in which derivatives can be constructed. Most often, peptide modification serves as a prelude to the more laborious total synthesis of a structural variant, as this approach allows much greater freedom in selection of the desired derivative. The quantitative conversion of methionine residues to the sulfoxide derivatives in α-chymotrypsin [Weiner, H., Batt, C. W., and Roshland, D. E., Jr. (1966) J. Biol. Chem. 241, 2687], trypsin [Holeysovsky, X., and Lazdunski, M. (1968) Biochim. Biophys. Acta 154, 457], ribonuclease [Jori., G., Galiazzo, G., Marzotto, A., and Scoffone, E. (1968) Biochim. Biophys. Acta 154, 1], and lysozyme [Jori., G., Galiazzo, G., Marzotto, A., and Scoffone, E. (1968) J. Biol. Chem. 243, 4272], yielded drastic conformation alterations in these enzyme structures. Selective S-methylation of myoglobin [Jones, W. C., Rothgeb., T. M., and Gurd, F. R. N. (1976) J. Biol. Chem. 251, 7452] and glucagon [Rothgeb, T. M., Jones, B. N., Hayes, D. F., and Gurd, R. S. (1977) Biochem. 16, 5813-5818] has been reported to destroy the native structure and, in the latter case, yielded peptide with less than 1% of the inherent activity of the native hormone. While, as indicated above, loss of native structure and/or activity is the usual consequence of methionine modification, much less frequently, acceptable substitutions for methionine have been constructed. Corradin, G. and Harburg, H. A. (1971) Proc. Nat'l. Acad. Sci. USA 68, 3036-3039, replaced a methionine in cytochrome C with a homoserine and observed a product with properties very similar to those of the parent heme protein. These scattered results indicate that no generalization may be made as to the distribution and/or role of methionine residues in proteins. Consequently, there was no reason to conclude that the single methionine residue in hpGRF could not be replaced, but every reason to suspect significant change in structure and near complete loss of activity. This expectation was fortified by the findings of Rivier et al., supra. Surprisingly, however, the compounds of the present invention, possessing a methionine substitution, exhibit substantial growth hormone releasing activity.

The methionine of hpGRF is, in accordance with this invention, replaced by a residue designated as X. The group X can be any of the following amino acid residues, each of which carries the L configuration: Met(O), Met(S-Me), Hse, Gln, Asn, Ser, Thr, Leu, Ile, Ala, Gly, Pro, Val, Phe, Trp, Tyr, Cys, Lys, Arg, His, Glu, and Asp.

Preferred subclasses of the group X are the following:
(1) Gln, Asn, Ser, Thr, Leu, Ile, Ala, Gly, Pro, Val, Phe, Trp, Tyr, Cys, Lys, Arg, His, Glu, and Asp.
(2) Gln, Asn, Ser, Thr, Leu, Ile, Ala, Lys, and Val.
(3) Gln, Ser, Thr, Leu, and Lys.
(4) Gln, Ser, and Leu.

Included in the compounds of this invention are their pharmaceutically acceptable non-toxic acid addition salts and their pharmaceutically acceptable non-toxic carboxylic acid salts.

The term "pharmaceutically acceptable non-toxic acid addition salts" encompasses both organic and inorganic acid addition salts including, for example, those prepared from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salts are those prepared from hydrochloric acid, acetic acid, or succinic acid. Any of the above salts is prepared by conventional methods.

The term "carboxylic acid salts" includes, for example, ammonium, alkali metal salts such as sodium, potassium, and lithium, and the like.

For the sake of convenience, the amino acids referred herein are described by their approved shorthand designations, either their three-letter or their single-letter designations.

These designations are as follows:

|  | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine sulfoxide | Met(O) | — |
| Methionine methylsulfonium | Met(S—Me) | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Using the convenient single-letter amino acid designation, the following peptides are illustrative of the compounds of this invention. Although not included in the compounds illustrated below, it will be recognized that each of the depicted compounds may be a free carboxylic acid or its corresponding amide.

Moreover, each of the compounds may be in the form of a pharmaceutically acceptable non-toxic acid addition salt and/or a pharmaceutically acceptable non-toxic carboxylic acid salt.

The following peptide sequence depict examples of the compounds of this invention:

Y-A-D-A-I-F-T-N-S-Y-R-K-V-L-G-Q-L-S-A-R-K-L-L-Q-D-I-A-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-R-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-N-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-D-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-C-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-E-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-Q-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-G-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-H-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-Hse-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-I-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-L-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-K-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-Met(O)-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-Met(S-Me)-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-F-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-P-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-S-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-T-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-W-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-Y-S-R-Q-Q-G-E-S-N-Q-E-R-G-A-R-A-R-L;

Y-A-D-A-I-F-T-N-S-Y-R-K-V-L-G-Q-L-S-A-R-K-L-L-Q-D-I-V-S-R-Q-Q-G-E-S-N-Q-E-R-G-A-R-A-R-L; and the like.

The compounds of this invention can be prepared by any of a variety of recognized peptide synthesis techniques including classical (solution) methods, solid phase methods, and the more recently available recombinant DNA methods. When the latter are employed, each of the amino acid residues, of course, must be naturally occurring.

Those compounds of this invention in which X is Met(O), Met(S-Me), or Hse, can be prepared from the corresponding Met-containing precursors by treatment with hydrogen peroxide, methyl iodide, or cyanogen bromide, respectively.

One of the principal methods for preparing the compounds of this invention is by the solid phase technique in which the amino acid sequence is constructed sequentially from an initial, insoluble, resin-supported C-terminal amino acid. Techniques for the solid phase method are described by J. Stewart et al., *Solid Phase Peptide Synthesis*, Freeman and Co., San Francisco, 1969.

In general, in the solid phase method, the amino acid corresponding to the C-terminal amino acid residue of the desired peptide is anchored to an insoluble resin support, and the peptide chain then is formed beginning at the resin-supported C-terminal amino acid. Individual amino acids are introduced sequentially until the desired amino acid sequence is obtained. Alternatively, small peptide fragments can be prepared and introduced into the peptide chain in the desired order. The peptide chain remains attached to the resin throughout synthesis, and, upon completion of the chain, the peptide is cleaved from the resin.

The peptide chain is attached to the polystyrene resin by means of an ester linkage formed between the carboxyl group of the C-terminal moiety and a specific methylene group present on the resin matrix as a site for such attachment. The polystyrene resin is a styrene polymer which is cross-linked by the addition of about 0.5 to about 3% divinylbenzene and which is chloromethylated or hydroxymethylated to provide sites for ester formation. An example of a hydroxymethylated resin is described by Bodanszky et al., *Chem. Ind.* (London) 38, 1597-98 (1966). A chloromethylated polystyrene resin is commercially available from Bio Rad Laboratories, Richmond, Calif. The resin is also described by Stewart et al., *Solid Phase Peptide Synthesis*, Freeman and Co., San Francisco, Calif., pp. 1-6.

The amino acids are coupled using techniques well-known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, isobutyl chloroformate, pivaloyl chloride, or like acid chlorides. Alternatively, the amino acid can be converted to an active ester such as a 2,4,5-trichlorophenyl ester, a pentachlorophenyl ester, a p-nitrophenyl ester, a N-hydroxysuccinimide ester, or an ester formed from 1-hydroxybenzotriazole.

Another coupling method involves use of a suitable coupling agent, such as N,N'-dicyclohexylcarbodiimide (DCC) or N,N'-diisopropylcarbodiimide (DIC). Other appropriate coupling agents will be apparent to those skilled in the art. [See Schroder and Lubke, *The Peptides*, Academic Press, 1965, Chapter III.]

It should be recognized that the α-amino group of each amino acid employed in the peptide synthesis must be protected during the coupling reaction to prevent side reactions involving the reactive α-amino function. It should also be recognized that certain amino acids contain reactive side-chain functional groups (e.g. sulfhydryl, ε-amino, carboxyl, and hydroxyl), and that such functional groups must also be protected both during the initial and subsequent coupling steps. Suitable protecting groups are known in the art [See for example, *Protective Groups In Organic Chemistry*, M. McOmie, Editor, Plenum Press, N.Y., 1973.]

In selecting a particular protecting group, certain conditions must be observed. An α-amino protecting group (1) must render the α-amino function inert under the conditions employed in the coupling reaction, (2) must be readily removable after the coupling reaction under conditions that will not remove side chain protecting groups and will not alter the structure of the peptide fragment, and (3) must eliminate the possibility of racemization upon activation immediately prior to coupling. A side chain protecting group (1) must render the side chain functional group inert under the conditions employed in the coupling reaction, (2) must be stable under the conditions employed in removing the α-amino protecting group, and (3) must be readily removable upon completion of the desired amino acid sequence under reaction conditions that will not alter the structure of the peptide chain.

It will be apparent to those skilled in the art that the protecting groups known to be useful for peptide synthesis will vary in reactivity to the agents employed for their removal. For example, certain protecting groups, such as triphenylmethyl and 2-(p-biphenylyl)isopropyloxycarbonyl are very labile and can be cleaved under mild acid conditions. Other protecting groups, such as t-butyloxycarbonyl, t-amyloxycarbonyl, adamantyloxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl, halobenzyloxycarbonyl, p-nitrobenzyloxycarbonyl, cycloalkyloxycarbonyl, and isopropyloxycarbonyl, are even less labile and require stronger acids, such as hydrogeun fluoride, hydrogen bromide, or boron trifluoroacetate in trifluoroacetic acid, for their removal.

Illustrative examples of amino acid protecting groups are set forth below.

A. For an α-amino group, protection may include (a) acyl-type groups, such as formyl, trifluoroacetyl, phthalyl, p-toluenesulfonyl (tosyl), benzenesulfonyl, nitrophenylsulfenyl, and the like; (b) aromatic urethane-type groups, such as benzyloxycarbonyl and substituted benzyloxycarbonyl, such as, for example, p-chlorobenzyloxycarbonyl, p-bromobenzyloxycarbonyl, p-nitrobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (c) aliphatic urethane-type groups such as t-butyloxycarbonyl, t-amyloxycarbonyl, isopropyloxycarbonyl, 2-(p-biphenylyl)isopropyloxycarbonyl, allyloxycarbonyl, and the like; (d) cycloalkyl urethane-type groups such as cyclopentyloxycarbonyl, cyclohexyloxycarbonyl, cycloheptyloxycarbonyl, adamantyloxycarbonyl, and the like; (e) thiourethane-type groups such as phenylthiocarbonyl; (f) alkyl-type groups such as triphenylmethyl, and (g) trialkylsilane groups, such as trimethylsilane. A preferred α-amino protecting group is t-butyloxycarbonyl (BOC).

B. For the ε-amino protecting group present in lysine, protection may be by any of the groups mentioned hereinabove for protection of an α-amino group. Typical groups include, for example, benzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl t-butyloxycarbonyl, isopropyloxycarbonyl, t-amyloxycarbonyl, cyclopentyloxycarbonyl, cyclohexyloxycarbonyl, cycloheptyloxycarbonyl, adamantyloxycarbonyl, p-toluenesulfonyl, and the like. The preferred ε-amino protecting group is o-chlorobenzyloxycarbonyl (ClBzl).

C. For the hydroxyl group of serine, threonine, or tyrosine, protection may be, for example, by $C_1$–$C_4$ alkyl, such as methyl, ethyl, and t-butyl; benzyl; substituted benzyl, such as p-methoxybenzyl, p-nitrobenzyl, p-chlorobenzyl, and o-chlorobenzyl; $C_1$–$C_3$ alkanoyl, such as formyl, acetyl, and propionyl; triphenylmethyl; or benzoyl. The preferred aliphatic hydroxyl protecting group is benzyl (Bzl), while the tyrosine aromatic hydroxyl is most commonly protected as a 2,6-dichlorobenzyl ether.

D. For the carboxyl group of aspartic acid or glutamic acid, protection may be, for example, by esterification using groups such as benzyl, t-butyl, cyclohexyl, cyclopentyl, and the like. The current groups of choice are cyclohexyl and cyclopentyl.

Upon completion of the desired peptide sequence, the protected peptide must be cleaved from the resin support, and all protecting groups must be removed. The cleavage reaction and removal of the protecting groups may be accomplished simultaneously or stepwise. When the resin support is a chloromethylated polystyrene resin, the bond anchoring the peptide to the resin is an ester linkage formed between the free carboxyl group of the C-terminal moiety and one of the many chloromethyl groups present on the resin matrix. It will be recognized that the anchoring bond can be cleaved by reagents which are known to be capable of breaking an ester linkage and of penetrating the resin matrix. One especially convenient method is by treatment with liquid anhydrous hydrogen fluoride. This reagent not only will cleave the peptide from the resin but will also remove all protecting groups. Hence, use of this reagent will directly afford the fully deprotected peptide. When it is desired to cleave the peptide without removing protecting groups, the protected peptide-resin can undergo methanolysis to give the protected peptide in which the C-terminal carboxyl group is methylated. The methyl ester can then be hydrolyzed under mild, alkaline conditions to give the free C-terminal carboxyl. The protecting groups on the peptide chain then can be removed by treatment with a strong acid, such as liquid hydrogen fluoride. A particularly useful technique for methanolysis is that of G. Moore et al., *Peptides,* Proc. 5th Amer. Pept. Symp., M. Goodman and J. Meinhofer Eds., John Wiley, N.Y., 1977, pp. 518–521, in which the protected peptide-resin is treated with methanol and potassium cyanide in the presence of crown ether.

Another method for cleaving the protected peptide from the resin is by ammonolysis or by treatment with hydrazine. If desired, the resulting C-terminal amide or hydrazide can be hydrolyzed to the free C-terminal carboxyl, and the protecting groups can be removed conventionally.

It will also be recognized that the protecting group present on the N-terminal α-amino group may be removed preferentially either before or after the protected peptide is cleaved from the resin support.

A typical preparation of amide compounds of the present invention by solid phase synthesis is achieved on a copolymer (styrene-2% divinylbenzene) benzhydrylamine resin, 100–200 mesh. The free benzhydrylamine level is determined by ninhydrin derivatization and nitrogen elemental analysis. In each step of the synthesis, the ratio of solvent to polystyrene is maintained at 10 ml. per each gram of resin. All amino acids are employed as their t-butyloxycarbonyl-protected amines. The benzhydrylamine is neutralized by two five-minute exposures to 5% v/v diisopropylethylamine in methylene chloride prior to initiating the first coupling reaction. Double coupling to ensure quantitative amidation is used for each amino acid addition. Two protocols for coupling are employed, depending upon the particular amino acid to be activated. Asparagine, glutamine, and arginine(tosyl) are coupled by the following procedure: (1) 5% diisopropylethylamine/methylene chloride, 2×2 minutes; (2) methylene chloride, 6×1 minute; (3) t-butyloxycarbonyl amino acid (3 equivalents), dicyclohexylcarbodiimide (3 equivalents), N-hydroxybenzotriazole (3 equivalents), dissolved in anhydrous N,N-dimethylformamide, 1×120 minutes; (4) methylene chloride, 6×1 minute; (5) repeat steps 1 through 4; (6) 50% trifluoroacetic acid in methylene chloride, 1×2 minutes; (7) 50% trifluoroacetic acid in methylene chloride, 1×20 minutes; (8) methylene chloride, 6×1 minute.

All other amino acids are attached by the following protocol: (1) 5% diisopropylethylamine/methylene chloride, 2×2 minutes; (2) methylene chloride, 6×1 minute; (3) t-butyloxycarbonyl amino acid (6 equivalents), dicyclohexylcarbodiimide (3 equivalents) dissolved in methylene chloride, 1×120 minutes; (4) methylene chloride, 6×1 minute; (5) repeat steps 1 and 2; (6) t-butyloxycarbonyl amino acid (3 equivalents), dicyclohexylcarbodiimide (3 equivalents), N-hydroxybenzotriazole (3 equivalents), dissolved in anhydrous N,N-dimethylformamide, 1×120 minutes; (7) methylene chloride, 6×1 minute; (8) 50% trifluoroacetic acid in methylene chloride, 1×2 minutes; (9) 50% trifluoroacetic acid in methylene chloride, 1×120 minutes; (10) methylene chloride, 6×1 minute. All amino acids being coupled to glutamine are coupled in anhydrous N,N-dimethylformamide. The side chain protected amino acids employed are arginine(tosyl), aspartic acid(β-cyclopentyl ester), tyrosine(2-bromobenzyloxycarbonyl), glutamic acid(γ-cyclopentyl ester), lysine(2-chlorobenzyloxycarbonyl), serine(benzyl ether), threonine (benzyl ether), and methionine(sulfoxide). All protecting groups except sulfoxide are removed concomitantly with cleavage of the peptide from the resin support using a 90:10 mixture of anhydrous hydrofluoric acid and p-cresol at 0° C. for 60 minutes. Methionine sulfoxide, if it is to be converted to methionine, is reduced following the peptidyl cleavage from the resin by treatment with 0.5M dithiothreitol at pH 7.0, 37° C. for 24 hours.

The compounds of this invention, when prepared by solid phase peptide synthesis, are initially purified by gel permeation chromatography on a G-50 superfine column in 10% v/v acetic acid at a linear flow rate of 10 cm/hour. Purification to homogeneity is achieved by reverse phase on a 0.46×25 cm Zorbax $C_8$ column, employing a linear gradient of acetonitrile in 0.1M ammonium phosphate, pH 7.2. The desired component is desalted on Sephadex G-25 in 0.01M ammonium bicarbonate, pH 8.5, and lyophilized.

Solid phase synthesis and purification of the α-carboxylic acid compounds of this invention is achieved as described above with the exception that synthesis is initiated on a copolymer (styrene-1% divinylbenzene) chloromethyl resin, 100–200 mesh.

Compounds of this invention can also be prepared via recombinant DNA methodology. In their preparation, a nucleotide sequence coding for the desired peptide is prepared using now routine methods for such synthesis. These methods generally involve preparation of oligonucleotides coding both for fragments of the desired coding sequence and for the complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a cloning vector at a location which permits the peptide product for which it codes to be expressed. A suitable cloning vector contains at least a portion of a gene's expression control sequence.

A typical expression control sequence can be described in terms of five elements. In the order in which they appear in the gene, the elements are as follows: (a) the promoter region; (b) the 5' untranslated region; (c) the protein coding sequence; (d) the 3' untranslated region; and (e) the transcription termination site.

The function of each of these elements in gene systems is well recognized. The promoter region mediates initiation of messenger RNA (mRNA) production (transcription). The promoter may be (1) free of external control (constitutive), (2) under the control of a repressor, a substance that, when present, represses gene function, or (3) under the control of an inducer, a substance that is required to induce gene function. The lipoprotein (lpp) gene, for example, is free from external control and thus is termed "constitutive".

Located at or near the promoter is the "transcription initiation site", a point at which RNA polymerase binds to initiate transcription of mRNA. Once transcription is initiated, mRNA is produced. The structure of the resulting mRNA is determined by the DNA sequences of the gene elements (b) to (d) above.

The resulting mRNA carries a sequence which is translatable into protein product. The translatable sequence is located downstream from the 5' untranslated region and upstream from the 3' untranslated region. Translation is mediated by the binding of ribosomes to a sequence in the mRNA 5' untranslated region denoted as the ribosome binding site and is initiated at the translation start codon (AUG) appearing as the first codon of the product gene sequence and coding as well for the amino acid methionine (Met). Translation terminates at one or more termination codons appearing at the end of the translation region.

By the techniques of recombinant DNA, it has become possible to prepare cloning vectors useful for the production of selected foreign (exogenous) proteins by inserting into such vectors an expression control sequence, i.e., a sequence of nucleotides that controls and regulates expression of structural genes with production of exogenous protein when operatively linked to those genes.

In the context of the foregoing, the term "expression control sequence" includes elements (a), (b), (d), and (e) above.

Recombinant DNA methodology can be employed to express compounds of this invention either as a portion of a larger "hybrid" molecule or by direct expression. In the direct expression mode, the cloning vector is designed such that the expression product is composed entirely of desired product preceded by a methionine (Met) residue resulting from the presence of the essential start codon. The superfluous Met residue can be removed by treating the product with cyanogen bromide or with phenyl isothiocyanate followed by a strong anhydrous acid, such as trifluoroacetic acid.

In the hybrid molecule expression mode, a DNA sequence coding for the desired product is inserted into the expression control sequence of a cloning vector at a point such that the product expressed comprises a hybrid protein. By "hybrid protein" as used herein is meant a recombinant DNA product comprising a foreign protein, generally all or a portion of the natural (endogenous) protein produced by the expression control sequence (for example, lipoprotein in the lipoprotein gene), to which is attached the desired protein.

The properly designed hybrid protein produced by recombinant DNA methodology will contain a cleavage site at the junction of the endogenous protein portion and the desired product. The cleavage site permits generation of mature product by chemical or enzymatic treatment of the hybrid protein product. Highly useful selective cleavage sites comprise a DNA sequence which codes for an amino acid or a sequence of amino acids which can be cleaved chemically or enzymatically at its C-terminal.

Examples of chemical agents useful for cleaving proteins are cyanogen bromide, BNPS-skatole, hydroxylamine, and the like. Cyanogen bromide cleaves proteins at the C-terminal of a methionine residue. Therefore, the selective cleavage site is a methionine residue itself.

Hydroxylamine cleaves at the C-terminal of the moiety -Asn-Z- in which Z is Gly, Leu, or Ala.

BNPS-skatole cleaves at the C-terminal of a tryptophan residue.

Examples of enzymatic agents useful for cleavage are trypsin, papain, pepsin, plasmin, thrombin, enterokinase, and the like. Each effects cleavage at a particular amino acid sequence which it recognizes.

An enzyme of choice is enterokinase. Therefore, a preferred selective cleavage site is that which enterokinase recognizes, viz., a DNA sequence coding for the amino acid sequence $-(Asp)_n-Lys-$ in which n is an integer from 2 to 4.

The most preferred selective cleavage site, since the compounds of this invention lack methionine, is a methionine residue. This residue, joined to the N-terminus of the desired product, is readily cleaved by known methods using cyanogen bromide to produce the desired mature product.

In constructing useful cloning vectors, several elements are required. Two of the required elements are common to all useful cloning vectors. First, the vector must have a DNA segment containing a functional origin of replication (replicon). Plasmids and phage DNA by their very nature contain replicons facilitating replication in a host cell.

Secondly, the vector must have a DNA segment which conveys to a transformable host cell a property useful for selection of transformed cells from non-transformed cells. Any of a wide range of properties can be used for selection purposes. One of the most commonly used properties is antibiotic resistance, e.g., tetracycline resistance or ampicillin resistance.

The foregoing two elements generally are present in readily available and recognized cloning vectors. Examples of suitable cloning vectors are bacterial plasmids, such as plasmids from *E. coli*, including pBR322, pMB9, ColE1, pCR1; wider host range plasmids, including RP4; phage DNAs, such as lambda, and the like. Most, if not all, of the above recognized vectors already carry the aforedescribed two elements.

A third element is the expression control sequence. Any of a wide range of such control sequences can be used including, for example, those from the lipoprotein gene, the β-galactosidase gene, the tryptophan gene, the β-lactamase gene, phage lambda, and the like.

In producing a suitable cloning vector by insertion of the selected expression control sequence, routine methods are used. Various sites exist within cloning vectors at which cuts can be made using a restriction endonuclease specific for such site. Any of these sites can be selected for insertion of the expression control sequence. As an example, in the well-recognized and documented plasmid pBR322, several suitable restriction sites exist, any of which may be employed as insertion sites. A PstI site is located within the gene for β-lactamase. Other sites outside of any specific coding region are EcoRI and PvuII. These and other sites are well recognized by those skilled in the art.

Taking advantage of any of these sites or others, insertion of an expression control sequence or the essential portion thereof can be readily accomplished in production of vectors defined by this invention.

A fourth element, of course, is the DNA sequence coding for the desired product. As previously noted, this DNA sequence can be constructed synthetically, e.g., using the recognized phosphotriester method or other well-recognized methods.

Suitable cloning vectors can be used in a wide range of host organisms, for example, gram-negative prokaryotic organisms such as *Escherichia coli*, Serratia, Pseudomonas, and the like; gram-positive prokaryotic organisms, such as Bacillus, Streptomyces, and the like; and eukaryotic organisms, such as Saccharomyces, and the like. Preferably, the host organism is a gram-negative prokaryotic organism. Of gram-negative prokaryotic organisms, *E. coli* is especially preferred, for example, *E. coli* K-12 strains, such as RV308.

Employing well recognized methodology, the appropriately prepared cloning vectors are used to transform suitable host organisms, are amplified in such organisms, and exogenous protein product is expressed using standard fermentation conditions. The exogenous protein product is isolated by routine methods from the resulting fermentation broth.

A typical procedure for product isolation from a Met cleavage site-containing precursor involves lyophilizing the product-containing cells. To one liter of 70% v/v formic acid then is added 10 grams of lyophilized fermentation solids. After dissolution (about 60 minutes) the solution is adjusted in cyanogen bromide concentration to 0.1M by the addition of 10.6 grams of reagent. Quantitative peptide cleavage amino-terminal to the desired product is complete in about 8 hours at 23° C.

The formic acid is removed by evaporation under vacuum, and the cleaved fermentation solids are lyophilized. The solids are dissolved at 10 grams/liter in 10% v/v acetic acid and applied to 5% of the column volume of a G-50 superfine Sephadex column (2.6×100 cm) flowing at a rate of 5 cm/hour, 4° C. Purification to homogeneity is achieved by reverse phase on a 0.46×25 cm Zorbax $C_8$ column, employing a linear gradient of acetonitrile in 0.1M ammonium phosphate, pH 7.2. The desired product is desalted on Sephadex G-25 in 0.01M ammonium bicarbonate, pH 8.5, and lyophilized.

The compounds of this invention, in view of their effect in stimulating release of growth hormone, have wide applicability. They can be used, for example, in treating primary dwarfism; short stature; wound healing; bone wasting diseases, such as osteoporosis; general catabolic states due to illness, trauma, or surgery; fracture healing; and the like. In addition, the compounds of this invention can be administered to farm animals, e.g., for milk production, in cattle; for growth in fowl, cattle, sheep, and pigs; and for neonatal pig survival.

The compounds of this invention can be used in a variety of pharmaceutical compositions and formulations and can be administered by a variety of conventional routes, such as intramuscular, intravenous, subcutaneous, intraperitoneal, and oral.

In administering the compounds of this invention parenterally or intraperitoneally, the pharmaceutical forms suitable for injection include sterile aqueous solutions or dispersions and sterile powders for reconstitution into sterile injectible solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating the compounds of this invention in the required amount of the appropriate solvent with various of the other ingredients, as desired.

If desired, and for more effective distribution, the compounds can be incorporated into slow release or targeted delivery systems such as polymer matrices, liposomes, and microspheres.

As noted, the compounds of this invention can also be administered orally. They can be used with an inert diluent or a pharmaceutical carrier which can take the form of capsules, tablets, suspensions, emulsions, solutions, dispersible powders, and the like. Moreover, the compounds of this invention can be administered either alone or as a mixture of a plurality of active ingredients.

Doses of the compounds of this invention are administered to the recipient for a period during which stimulation of the release of growth hormone is desired. The weight of the recipient and mode of administration will have an influence upon the size of the dose necessary to induce a particular response.

It is especially advantageous to formulate the compounds of this invention in unit dosage form for ease of administration and uniformity of dosage. Unit dosage form as used herein refers to a physically discrete units suited as unitary dosages for the subject to be treated. Each unit contains a predetermined quantity of the compound calculated to produce the desired therapeutic effect in association with the pharmaceutically acceptable carrier. The specific unit dosage form is dictated by and directly dependent upon (a) the unique characteristics of the particular composition and (b) the particular therapeutic effect to be achieved.

The following examples are illustrative of this invention. They are not intended to be limiting upon the scope thereof.

EXAMPLE

Preparation of Derivatives of hpGRF

One mg of hpGRF, obtained from Peninsula Laboratories, was solubilized in one ml of 0.01M hydrochloric acid (pH 2.5). The solution was divided into four equal aliquots, and each was diluted to a concentration of 0.5 mg hpGRF/ml by the addition of 250 μl of 0.01M HCl. The first aliquot was removed and stored at 22° C. for the duration of the experimentation, to serve as a control. Analysis of the control and the extent of each respective chemical modification with hydrogen peroxide, cyanogen bromide, and methyl iodide, described hereinbelow, was performed by high performance liquid chromatography (HPLC). Quantitation was achieved by peak height measurement at 214 nm, of a symmetrical peak eluting at 10 minutes from a (0.46×25 cm) Zorbax $C_8$, 150 Angstrom reverse phase column, at 45° C. in 0.1M ammonium phosphate buffer, pH 7.2/27.5% 1-propanol, v/v. Over the six hours of experimentation, the control solution exhibited no change in peak elution time or height. Each modification reaction was quenched by a 5:1 dilution (hpGRF final concentration of 0.1 mg/ml) with addition of two ml of 0.1M methionine/0.01M HCl, pH 3.5. Samples were divided and stored at −20° C. and 4° C. prior to analysis of biological activity.

A. Preparation of hpGRF[Met(O)-27]

Fifty ml of a 1M hydrogen peroxide solution in 0.1M hydrochloric acid was added to one of the four aliquots described above. The reaction was monitored by HPLC and found to occur rapidly with a $t_{\frac{1}{2}}$ of 30 minutes. The sulfoxide derivative elutes from the reverse phase column 2.5 minutes earlier than hpGRF. By peak height quantitation and the absence of any other apparent impurities, the hpGRF methionine sulfoxide-27 product is estimated to be greater than 90% pure.

B. Preparation of hpGRF[Met(S-Me)-27]

Five μl of methyl iodide were added to one of the four previously described aliquots. The reaction was monitored by HPLC and found to move slower than the hydrogen peroxide oxidation. A total reaction time of six hours was necessary to diminish the starting material to less than 1% of its original peak height. The hpGRF methionine(S-methyl)-27 was observed to elute from the Zorbax $C_8$ column at 10 minutes, employing 37.5% acetonitrile/0.1M ammonium phosphate, pH 7.2, 45° C. No other derivatives were observed through gradient analysis; it was concluded that the methylated product was greater than 90% pure.

C. Preparation of hpGRF[Hse-27]

Fifty μl of a 1M cyanogen bromide solution in 0.1M hydrochloric acid were added to one of the four previously described aliquots. The $t_{\frac{1}{2}}$ for disappearance of the starting material was 70 minutes. Two peaks, poorly resolved from each other, were observed in nearly equal concentration, increasing in size with each decrease in concentration of the starting peptide and at approximately 2.5 minutes earlier elution than the starting material. At a 23.5% acetonitrile concentration, the two peaks were clearly separable, and the later eluting component was identified as the methionine sulfoxide derivative by dilution with the previously prepared product produced by $H_2O_2$ oxidation. The earlier eluting derivative at approximately 50% purity is believed to be the desired hpGRF homoserine-27, since HPLC analysis for the 28-44 and 1-27 cyanogen bromide cleavage fragments was negative. Similar cleavage of the starting material in 70% formic acid and 1N hydrochloric acid generated the homoserine intact peptide in 40 and 60% yields, respectively, with no apparent formation of the sulfoxide product. The remaining hpGRF under the more acidic conditions was observed to be cleaved to the 1-27 and 28-44 peptide fragments.

We claim:

1. A compound having the formula H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-X-Ser-Arg-Gln-Gln-Gly-Glu-Ser-Asn-Gln-Glu-Arg-Gly-Ala-Arg-Ala-Arg-Leu-Y in which Y is OH or $NH_2$ and X is selected from the group consisting of Met(O), Met(S-Me), and Hse and pharmaceutically acceptable salts thereof.

2. Compound of claim 1, in which Y is OH.

3. Compound of claim 1, in which Y is $NH_2$.

4. Compound of claim 1, in which X is Met(O) and Y is $NH_2$.

5. Compound of claim 1, in which X is Met(S-Me) and Y is $NH_2$.

6. Compound of claim 1, in which X is Hse, and Y is $NH_2$.

* * * * *